(12) United States Patent
Kell

(10) Patent No.: US 8,069,856 B2
(45) Date of Patent: Dec. 6, 2011

(54) DYNAMIC INFANT HEAD SUPPORT

(75) Inventor: Jessica Joy Kell, Chesapeake, VA (US)

(73) Assignee: Jessica Joy Kell, Chesapeake, VA (US)

( * ) Notice: Subject to any disclaimer, the term of this patent is extended or adjusted under 35 U.S.C. 154(b) by 242 days.

(21) Appl. No.: 11/902,110

(22) Filed: Sep. 19, 2007

(65) Prior Publication Data
US 2009/0070938 A1    Mar. 19, 2009

(51) Int. Cl.
*A61G 15/00* (2006.01)
*A61F 5/37* (2006.01)
*A47C 20/00* (2006.01)

(52) U.S. Cl. ............... 128/845; 128/846; 5/655; 5/645; 5/644; 5/636

(58) Field of Classification Search ............. 128/118.1, 128/845, 846, 848; 5/636, 644, 645, 655, 5/655.3; 602/13; D24/183; 2/410; 601/39
See application file for complete search history.

(56) References Cited

U.S. PATENT DOCUMENTS

| | | | |
|---|---|---|---|
| 1,795,693 A | | 3/1931 | Rosett |
| 2,531,074 A | | 11/1950 | Miller |
| 2,676,587 A | | 4/1954 | Corcoran |
| 2,896,612 A | | 7/1959 | Bates et al. |
| 3,094,118 A | | 6/1963 | De Besme et al. |
| 3,159,160 A | | 12/1964 | Ullom |
| 3,848,281 A | * | 11/1974 | Mathews ............ 5/636 |
| 4,248,215 A | | 2/1981 | Bleakley |
| 4,777,679 A | * | 10/1988 | DeLooper ............ 5/655.3 |
| 5,094,229 A | | 3/1992 | Pomatto et al. |
| 5,211,162 A | * | 5/1993 | Gillen et al. ............ 601/149 |
| 5,257,429 A | * | 11/1993 | Genis ............ 5/636 |
| 5,638,565 A | * | 6/1997 | Pekar ............ 5/710 |
| 5,642,544 A | * | 7/1997 | Munoz ............ 5/644 |

(Continued)

OTHER PUBLICATIONS

American Academy of Pediatrics. American Academy of Pediatrics AAP Task Force on Infant Positioning and SIDS: Positioning and SIDS. Pediatrics. 1992:89; 1120-1126.
Fish, Deanna and Dulcey Lima. "An Overview of Positional Plagiocephaly and Cranial Remolding Orthoses." Journal of Prosthetics and Orthotics 2003: 15 (2); 37-47.

(Continued)

*Primary Examiner* — Patricia Bianco
*Assistant Examiner* — Victoria J Hicks
(74) *Attorney, Agent, or Firm* — Stein McEwen, LLP

(57) ABSTRACT

A dynamic infant head support for preventing, or correcting, the abnormal shape of a head of an infant, and a method of using the support for treating deformational plagiocephaly. The support is an oval-shaped pillow, with a central opening to receive the head of the infant to be treated. Spaced barriers divide the interior of the pillow into a plurality of compartments. A ring-like manifold passes through the interior of the pillow and communicates with each compartment. A plurality of valves is operatively associated with the manifold; one valve is located in each compartment. The valves allow fluid, such as pressurized air, in the manifold, to inflate individual compartments. The manifold is pressurized by a pump, at a remote location; a heater warms the pressurized air. A remote controller is connected to the valves by electrical leads. The controller governs the sequence of operation of the valves, and regulates the duration of time that each valve is open. The controller may be programmed, to inflate or expand the compartments in the pillow, to gently lift, and mildly turn, the head of the infant positioned thereon, thus combating the abnormal shape or deformation.

1 Claim, 7 Drawing Sheets

U.S. PATENT DOCUMENTS

| | | | | |
|---|---|---|---|---|
| 5,813,066 | A | * | 9/1998 | Gebhard et al. .................. 5/655 |
| 5,951,503 | A | | 9/1999 | Pomatto |
| 6,039,704 | A | | 3/2000 | Domenighini et al. |
| 6,131,219 | A | * | 10/2000 | Roberts .............................. 5/644 |
| 6,336,907 | B1 | * | 1/2002 | Dono et al. .................... 601/150 |
| 6,386,201 | B1 | * | 5/2002 | Fard .............................. 128/848 |
| 6,423,019 | B1 | | 7/2002 | Papay et al. |
| 6,428,494 | B1 | | 8/2002 | Schwenn et al. |
| 6,592,536 | B1 | | 7/2003 | Argenta |
| 6,715,171 | B2 | * | 4/2004 | Grabe ............................... 5/644 |
| 6,939,316 | B2 | | 9/2005 | Sklar et al. |
| 2006/0161200 | A1 | | 7/2006 | Fallah |
| 2007/0061976 | A1 | * | 3/2007 | Bazargani ......................... 5/644 |
| 2007/0240723 | A1 | * | 10/2007 | Hong et al. .................. 128/848 |

OTHER PUBLICATIONS

Graham, J. et al. "Management of Deformational Plagiocephaly: Repositioning versus Orthotic Therapy." The Journal of Pediatrics. Feb 2005: 146(2); 258-62.

Hutchinson, Lynne B., John M.D. Thompson and Ed A. Mitchell. "Determinants of Nonsynostotic Plagiocephaly: A Case Control Study." Pediatrics. Oct. 2003:e316.

Littlefield, Timothy R. "Car Seats, Infant Carriers, and Swings: Their Role in Deformational Plagiocephaly." Journal of Prosthetics and Orthotics 2003: 15(3); 102-6.

Littlefield, Timothy R., Jacque Reiff and Harold Rekate. "Diagnosis and Management of Deformation Plagiocephaly." BNI Quarterly, 2001: 17(4); 1-9.

* cited by examiner

DYNAMIC INFANT HEAD SUPPORT

TECHNICAL FIELD

This invention pertains to an apparatus and method for preventing, inhibiting progression of, and/or correcting plagiocephaly, an abnormal shape of the head of a human, usually an infant. The invention relates to a dynamic head support with sequential inflation and deflation of its compartments to provide variable external light pressures to the cranial vault and gentle changes in head position.

BACKGROUND OF THE INVENTION

The cranium, or skull, of a human infant is made up of several bone plates bridged by compliant membranous separations, known as sutures. These sutures solidify to herald the completion of rapid brain growth at eighteen to twenty-four months of age. Normally, the infant skull is symmetrical in shape. However, the shape of the head may be influenced by in utero constraint, external pressures during the birth process, as well as modeling and gravitation forces on the rapidly developing skull of an infant after birth. A condition known as occipital positional plagiocephaly, or deformational plagiocephaly, results in an asymmetrical head. This abnormal skull is most often a classic parallelogram or rhomboid shape, with bulging of the forehead and forward displacement of one ear as well as facial asymmetry, when observed from a top down or plan view.

Approximately one out of every three hundred healthy birth infants have a noticeable flattening of the head, asymmetry of the skull base and face, or both. Risk factors for plagiocephaly include prematurity, multiple births (twins, triplets), congenital anomalies, neurological injury, delayed muscle and motor development, tumors, and cervical defects.

Positional plagiocephaly has had an increased incidence since 1992 when the American Academy of Pediatrics initiated the "Back to Sleep" campaign, encouraging the placement of infants on their backs instead of their stomachs for sleeping purposes. The campaign reduced the occurrence of sudden infant death (SIDS), but led to a notable escalation in the number of plagiocephalic children. Another factor that may have contributed to the greater incidence of deformational plagiocephaly is increased usage of car seats, infant carriers, baby swings, "bouncy seats," strollers, cribs and stationary toy gyms. Yet other factors may include feedings and social interactions that are routinely offered from the same side of the infant, as well as a preferred position when carrying the child.

Dysfunction of the neck musculature is almost universally associated with plagiocephaly. Neck abnormality, such as torticollis, is one important cause of plagiocephaly; likewise, existing skull deformity predisposes to torticollis and other forms of neck imbalance. Long term problems associated with plagiocephaly include subtle cerebral dysfunction (language disorders, learning disability, attention deficits and disorders of processing sensory stimulation), various functional disabilities caused by facial and jaw asymmetry, and psychosocial issues such as depression and tainted self-image.

Early assessment, diagnosis, and rehabilitation of plagiocephaly have been prerequisites for successful treatment to date. The value of education of caregivers, hospital personnel, and parents about the importance of alternating infant sleeping and feeding orientations should not be overlooked. Additionally, supervised "tummy time" for infants continues to be encouraged. Since 80% of postnatal brain growth, which can direct head shape, occurs early in life, plagiocephalic patients under the age of 18 months are also often given active and passive neck stretching exercises, to perform regularly, as the first line of treatment.

Helmet therapy, or use of external cranial remodeling orthotic devices, has been used alone and as an adjunct treatment option for plagiocephaly. These orthotic devices are predicated upon the theory that pressure from a rapidly growing brain against a concave surface will round flattened or deformed areas caused by earlier pressure against a flat surface. The optimum response for orthotic helmets, bands and caps is said to occur at ages of 4-12 months, which represents the period of greatest malleability of the skull bone, with the normalizing effect of rapid brain growth. Nonetheless, 25% of infants 3-6 months of age, 70% of infants 6-18 months of age, and 100% of older children undergo surgical correction for progression of the condition.

An orthotic helmet for treating deformational cranial asymmetry is shown in U.S. Pat. No. 4,776,324, granted to S. K. Clarren, on Oct. 11, 1988. The dimensions of the therapeutic helmet cavity are prescribed in relation to specific CT scan sections of the plagiocephalic infant's cranium, as shown in FIGS. 3 and 4 of the Clarren patent. A graded series of sized helmets is provided for such treatments. Each helmet cavity is configured to accommodate and treat infants of specified ages and degrees of plagiocephaly.

Orthotic bands, or caps, for remodeling the cranium are disclosed in U.S. Pat. No. 5,951,503, granted Sep. 14, 1999 to Jeanne K. Pomatto, and U.S. Pat. No. 6,423,019, granted Jul. 23, 2002, to Francis Papay et al. Each band provides at least one recess into which the skull may be remodeled as it grows. The orthotic band of Papay et al further includes at least one expandable bladder, on the inner wall of the band.

Other orthotic devices are disclosed in U.S. Pat. No. 5,094,229, granted Mar. 10, 1992, to Jeanne K. Pomatto et al, and U.S. Pat. No. 6,428,494, granted Aug. 6, 2002, to Stannon F. Schwenn et al.

Despite some advances in cranial remodeling, these prior art appliances are costly, uncomfortable and unsightly to wear and difficult to retain in position. Moreover, these devices require both complex measures to accommodate each individual patient as well as the intervention of skilled doctors, educators, and trained medical personnel.

The key to successful management of deformational plagiocephaly is prevention of its occurrence altogether. A number of devices have been used with the goal of preventing early skull deformation including contour pillows, foam pads with cut-outs of varying sizes, and static infant positioning devices. However, none of these devices present dynamic options that also alter orientation of the infant's head to reduce "side preference," favored head orientation by the infant which fosters progressive neck imbalance and skull deformity. Furthermore, all of the known devices and techniques also necessitate the costly involvement of knowledgeable, skilled care providers and educators to achieve satisfactory results.

The requirement for a simple, yet effective, dynamic head support that prevents deformational plagiocephaly, while obviating the need for skilled care providers and frequent intervention, remains unfulfilled.

SUMMARY OF THE INVENTION

In view of the shortcomings of known static devices for treating positional skull deformities, the present invention provides a dynamic head support comprising an oval or doughnut-shaped pillow with a central opening, for effectively mitigating plagiocephaly. The pillow should be formed of a pliable, elastomeric material that allows for inflation and deflation, but may also have other desirable properties such as a non-latex outer contact surface that is hypoallergenic, waterproof, heat-resistant/flame retardant, and antibacterial or washable for hygienic use with subsequent patients.

The pillow comprises a plurality of separate compartments, which are inflated and deflated individually and sequentially. The center of the pillow, which receives the base of the skull of the infant, can remain open to the surface below or it may house a loose fitting fabric sling across the opening as long as this covering provides virtually no external pressure upon the infant's head.

In the preferred embodiment, a central ring of tubing, or a manifold, is located in the interior of the pillow, and forced air is delivered throughout the pillow via the manifold. The manifold can be fabricated of rigid or semi-rigid rubber, plastic or metal. A network of individual air tubes branches out of the central ring of tubing; each individual tube services one of the compartments. A reversible pump delivers and evacuates forced or pressurized air to and from distinct pillow compartments.

Pillow compartments are recruited in an alternating pattern by means of solenoid valves located in each compartment that open (unclamp) or close (clamp) each of the individual air tubes in accordance with a computerized program. The inflatable compartments expand from below and slightly inward toward the skull in order to make enough contact with the head to apply a gentle external pressure that is also capable of subtly lifting and/or delicately rotating the head. Compartments are ideally inflated individually for a specified time period, but may also be recruited as adjacent pairs, multiple sections, or all of them together. The valves, located proximal to the main central ring or manifold, are in a closed or clamped position at baseline and, thus, the pillow compartments are deflated.

When a valve is programmed to open an air tube, the compartment it empties into receives air pressure and subsequently expands. The compartment is decompressed via the reversible pump after a preset inflation interval. Sequential inflation and deflation of the individual compartments prevent constant molding pressures from being exerted on the skull, while gentle manipulation of the child's head also defeats the development of preferential head orientation by the infant. Movement of the subject's head is accomplished by gradual inflation and a defined degree of compartment expansion to simulate careful manual manipulations, particularly for the fragile premature, post-surgical or critically ill patient, often intubated with a breathing tube for respiratory assistance or otherwise particularly sensitive to abrupt stimulation.

In a first alternative embodiment, the manifold as well as the branched individual air tubes and corresponding solenoid valves are located exterior to the pillow. In this arrangement, each air tube is individually attached to the pillow, prior to use, via a common coupling on the outer edge of a corresponding compartment. This arrangement allows for the availability of a single external assembly (manifold with compatible tubing and valves) to universally accommodate different pillows. This embodiment also provides for easier maintenance or replacement of necessary parts.

Rather than using forced air to expand and contract the walls of the compartments, a different fluid or gel medium, or mechanical devices, can alternatively be used.

The outer surface of each compartment may include multiple soft, tiny projections or slightly raised air cells that aid in the gentle movement of the infant's head, while comfortably massaging same. Alternatively, the pillow surface may be smooth, allowing for a replaceable covering or sleeve to envelop it.

The oval shape of the pillow is significant, for the lower edge of the pillow provides natural support of the neck region of the supine infant or patient. The pillow may also be used in conjunction with a torso-stabilizing wedge to preclude the infant from rotating to a prone position, a potential suffocation risk. Alternatively, the head support can be fastened to a virtually flat, but flexible, cushioned rectangular base that lies below the infant's shoulders to approximately the mid-back of the child, such as by providing Velcro (hook and loop) attachments between the back of the pillow and the flat base. With this arrangement, the device supports attachable soft bolsters to secure the shoulders in supine position and allows the device to also be more easily positioned and secured for use in the seat of a stroller, baby swing or other infant apparatus. An attached foam ring base, extending around the entire circumference on the underside of the pillow to provide additional structure and support, is also contemplated.

The forced air may also be warmed to soothe the premature infant and assist in regulating body temperature.

Power for operating the pump delivering forced air to the selected pillow compartments may be supplied by a battery, or from a plug-in outlet in the wall of a building. The plug cord may be of a predetermined length or of a known retractable design. For further ease of use, the power switch can be illuminated or activated and deactivated by remote control.

The present invention represents a versatile device that can be produced in varying sizes appropriate for premature infants through the age of approximately one year, based on normalized head circumference chart averages. A second alternative embodiment employs two or more concentric head support pillows, with a separate set of compartments corresponding to distinct manifolds. In effect, this embodiment constitutes a smaller diameter head support surrounded by a larger head support. The advantage of pairing different-sized complete head supports together is the ability to service numerous patients, with diverse head sizes, with the availability of a single, readily adaptable device. The smaller and most interior pillow employs an interior assembly of manifold, valves and tubes while the larger, outermost pillow or pillows utilizes an exterior assembly of manifold, valves and tubes. The appropriate pillow and associated assembly is selected based on the head size of the patient. The inner head support is arranged in a slightly lower or depressed plane relative to the plane of the outer head support. Therefore, when the inner head support is not in use it does not interfere with the functioning of the outer head support because of its position below the patient's head within the central opening of the outer pillow. When use of the inner head support is favored, the entire device is inverted to expose a now slightly elevated inner head support surrounded by a deflated outer head support. Similarly, in this orientation, there is no interference of the inner head support function by the idle outer head support.

The dynamic head support is suitable for use in a hospital setting for patients subject to prolonged supine positioning, such as in an intensive care unit setting or during general anesthesia, as well as for home use. The basic principles of the invention may also be useful for older children, and even adults, with neurological injury, chronic illness, or other disabilities.

The envisioned method is one of treating head deformities in infants and young children in a simple, effective manner, relying upon selective inflation of compartments within the dynamic head support to gently lift and mildly turn the head, without the frequent intervention of skilled personnel. The method can be implemented by a controller, of known design, that can be programmed to govern the inflation, and deflation, of selected compartments within the pillow. Reversible inflation/deflation pumps, as well as the solenoid valves, are well understood by those skilled in the art and are also readily commercially available. Moreover, these pumps and controllers are manufactured in convenient sizes that can be opportunely attached to a bedside, infant isolette or crib, or even be incorporated as an integral part of the head support itself.

Other objectives realized by the dynamic head support with individually inflatable compartments will be gleaned from the appended drawings and the accompanying specifications.

DETAILED DESCRIPTION OF THE PREFERRED EMBODIMENT

Figure 1:
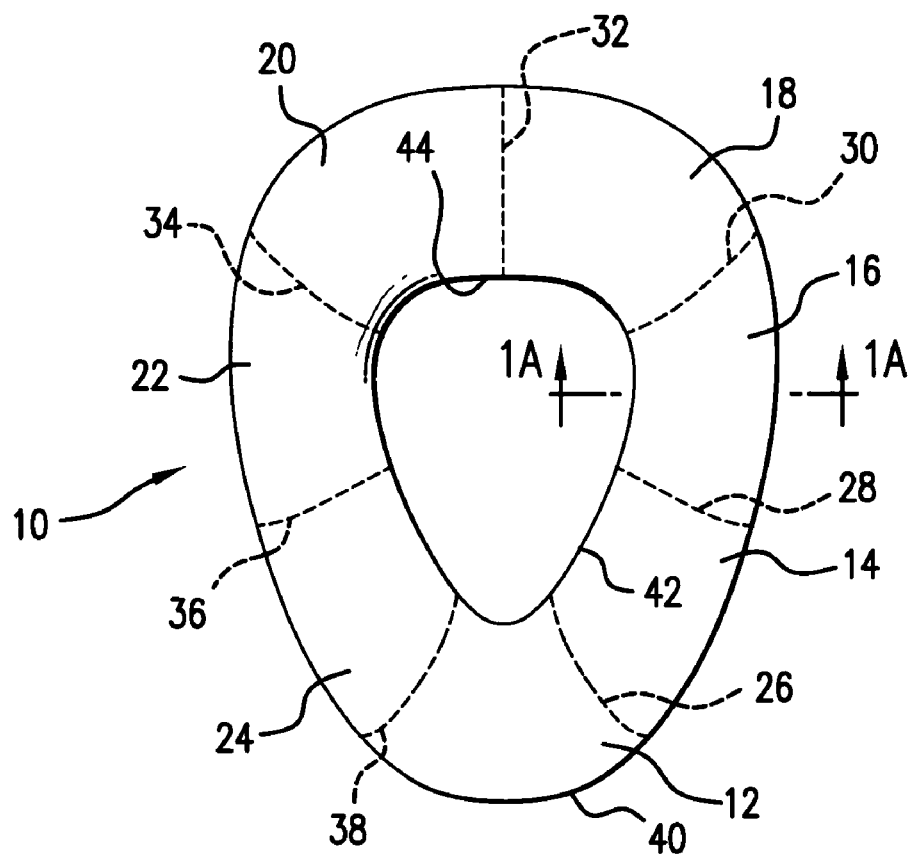
FIG. 1 is a top plan view of the preferred embodiment of a dynamic infant head support constructed in accordance with the principles of the present invention.

FIG. 1 depicts the unique dynamic infant head support 10, or pillow. Support 10 is an oval or doughnut-shaped ring and includes seven compartments 12, 14, 16, 18, 20, 22 and 24 of approximately equal size. Barriers 26, 28, 30, 32, 34, 36 and 38 separate the compartments from one another. The dimensions of each compartment are defined by a first barrier, a second adjacent barrier, an outer wall and an inner wall. To illustrate, compartment 12 is defined by barrier 38 and barrier 26, and by outer wall 40 and inner wall 42. An oval-shaped opening 44 is formed in the interior of head support 10. The oval shape of head support 10 ensures that compartment 12, at the base of the support, adequately supports the neck of an infant in a supine position.

Figure 1A:
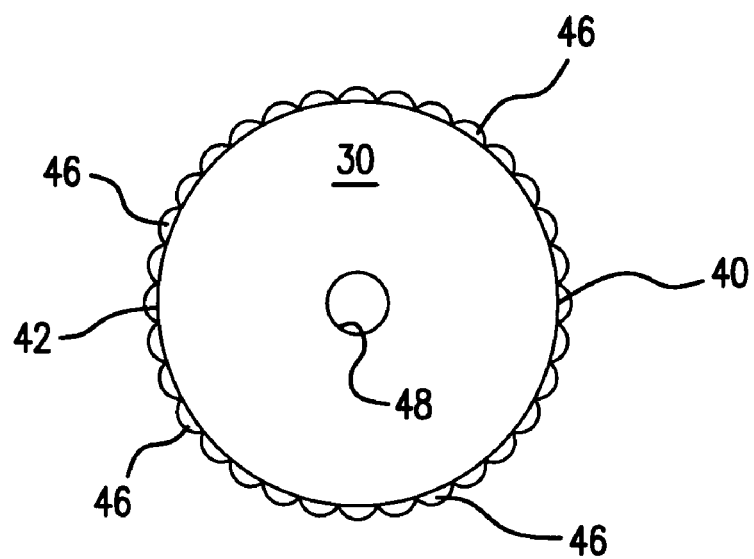
FIG. 1A is a vertical cross-sectional view through the dynamic infant head support of FIG. 1, such view being taken along line 1A-1A, and in the direction indicated.

FIG. 1A shows a vertical cross-sectional view through the dynamic infant head support of FIG. 1, such view being taken along line 1A-1A, and in the direction indicated. A central aperture 48 is defined in barrier 30, and a similar aperture is formed in every barrier, to allow for passage of a tubing manifold.

This figure also exemplifies projections 46 that may extend around the circumference of support 10. The projections may assume the form of semi-circular air-filled "bubbles," tiny fingers or similar protuberances. Projections 46 may be limited to those areas of support 10 that engage the head of the infant resting upon support 10.

Support 10 is fabricated of a pliable material that may also be non-latex, hypoallergenic material that is heat resistant and flame retardant. The material may also be washable, or covered by a removable, washable or disposable sleeve or covering which may be slipped over support 10. A new sanitary sleeve or covering (not shown) may be used whenever desired, or for each new patient, during the extended life of support 10.

Figure 2:
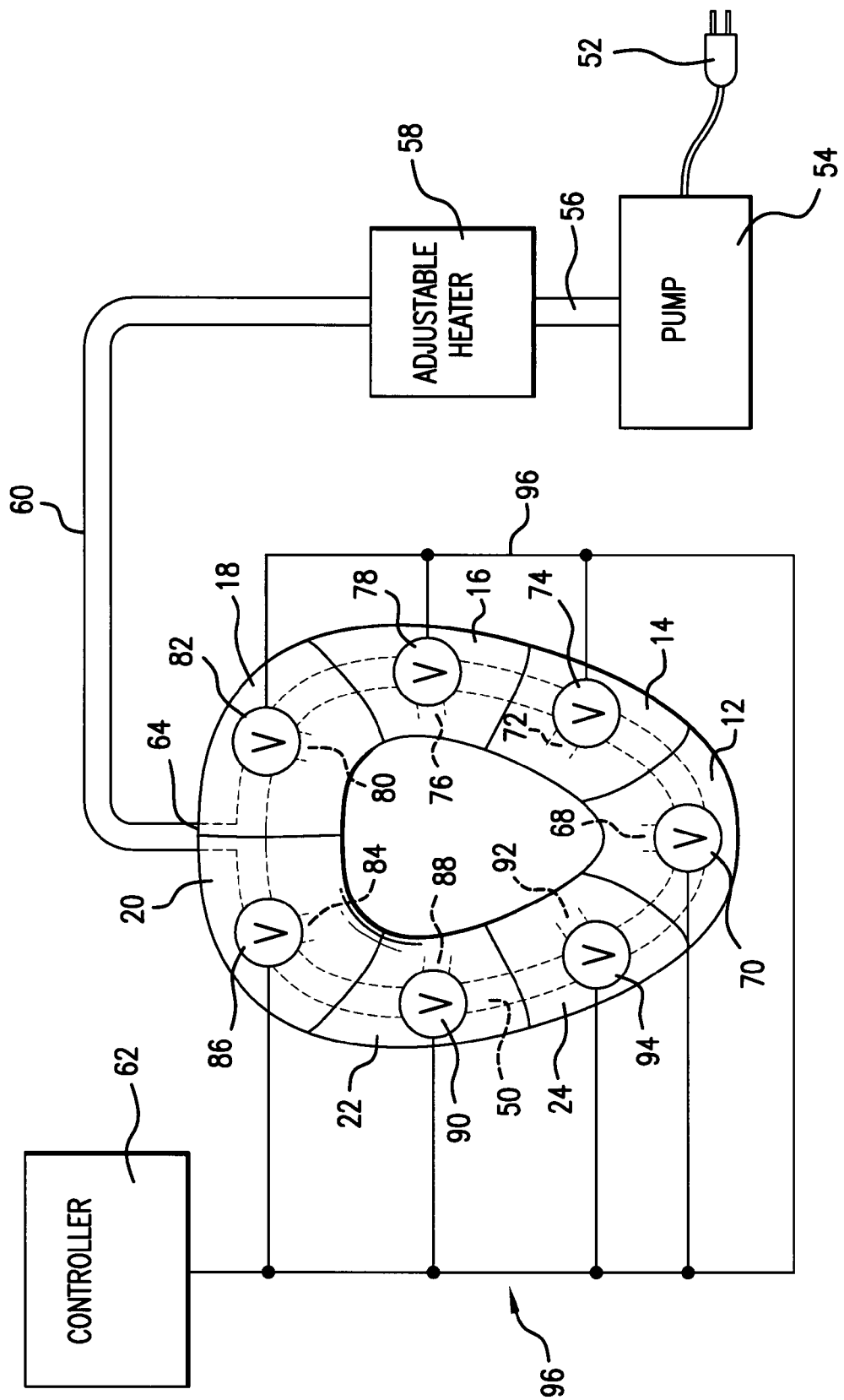
FIG. 2 is a schematic view of the preferred embodiment of a system for inflating the dynamic infant head support of FIG. 1.

FIG. 2 shows, schematically, the system for selectively, and sequentially, inflating the individual compartments 12, 14, 16, 18, 20, 22 and 24 within head support 10 in accordance with the description of the preferred embodiment. A manifold 50, that is generally oval-shaped, is shown in dotted outline in FIG. 2. Manifold 50 passes through an aligned aperture in each barrier, so that the manifold is seated within the interior of head support 10. Aperture 48 in barrier 30 is illustrative of such feature, and an aperture is present in each barrier.

The system for pressurizing the head support 10 includes pump 54, which receives power from plug 52 that is inserted into an electrical receptacle (not shown), conduit 56 which delivers the pressurized air from pump 54 to heater 58, and central tubing 60 which delivers the air to manifold 50 for distribution to the pillow compartments. Heater 58 is of conventional design, and may be adjusted over a temperature range of 32°-40° C. The gently heated air from heater 58 soothes the infant while assisting in body temperature regulation, particularly beneficial for a newborn or premature infant.

Controller 62 includes a program (not shown) for operating the solenoid valves associated with manifold 50 in a predetermined pattern. The controller operates the valves in head support 10 in a particular pattern or sequence for specific durations of time. The pressurized air flows through conduit 60 and enters inlet port 64 of head support 10.

First branch tube 68, with valve 70 operatively associated therewith, governs the inflation of compartment 12. Second branch tube 72, with valve 74 operatively associated therewith, governs the inflation of compartment 14. Third branch tube 76, with valve 78 operatively associated therewith, governs the inflation of compartment 16. Fourth branch tube 80, with valve 82 operatively associated therewith, governs the inflation of compartment 18. Fifth branch tube 84, with valve 86 operatively associated therewith, governs the inflation of compartment 20. Sixth branch tube 88, with valve 90 operatively associated therewith, governs the inflation of compartment 22. Lastly, seventh branch tube 92, with valve 94 operatively associated therewith, governs the inflation of compartment 24. An electrical conduit, indicated generally by reference numeral 96, includes individual leads extending to each one of the valves in the separate compartments and provides the electrical force to operate each valve.

Controller 62 operates valves 70, 74, 78, 82, 86, 90 and 94, so that each compartment within head support 10 may be individually pressurized. The valves may be solenoid valves, and may be operated by a remote electrical signal passing from controller 62 via electrical conduit 96, in a known manner. The valves are normally biased closed, thus retaining head support 10 in a deflated condition. Upon opening any one of the valves, the pressurized air fills the related branch tube and associated compartment. To illustrate, if valve 70 is opened, the pressurized air from manifold 50 flows through branch tube 68 to fill compartment 12 and inflate same. Similar relationships hold true for filling compartments 14, 16, 18, 20, 22 and 24 via their related branch tubes.

Pump 54 also governs the deflation of the selected compartment. Pump 54 is reversible in operation, and withdraws air from an inflated compartment to deflate same. The air withdrawn from the selected compartment via the branch tubes and manifold 50 is coordinated with the opening and closing of the valves in each compartment.

Figure 3A:
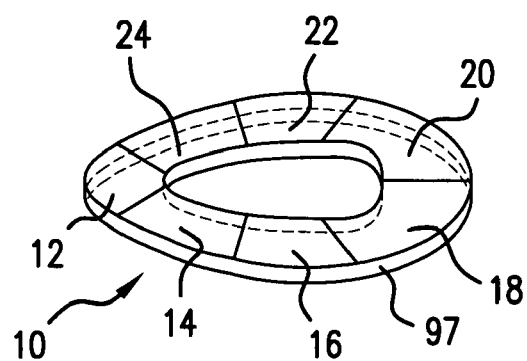
FIG. 3A shows the dynamic infant head support of FIG. 1 in deflated condition.
Figure 3B:
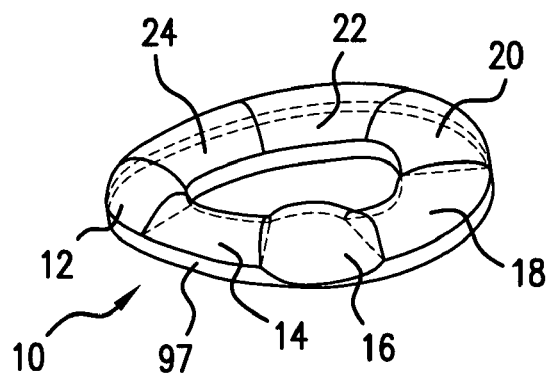
FIGS. 3B, 3C and 3D show different compartments within the dynamic infant head support in inflated condition.
Figure 3C:
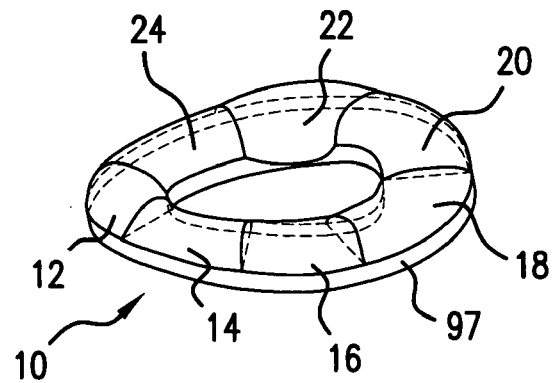
Figure 3D:
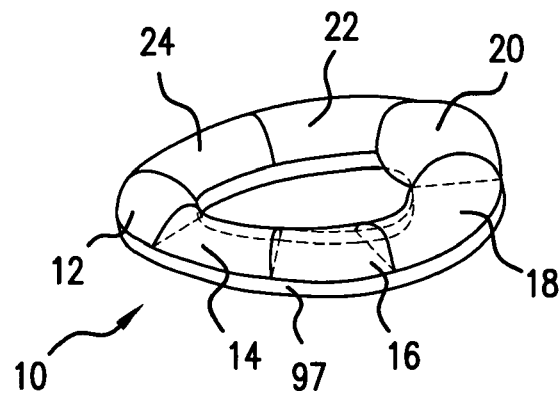

FIG. 3A shows head support 10 in its deflated condition, while FIG. 3B shows compartment 16 in its inflated condition. FIG. 3C shows compartment 22 in its inflated condition, while FIG. 3D shows compartment 20 in its inflated condition. The system for selectively inflating the compartments of head support 10 is visible in FIG. 2, but is absent from FIGS. 3A-3D. Here is also illustrated an optional attached foam ring base 97 extending around the entire circumference on the underside of the pillow to provide additional structure and support.

Figure 4:
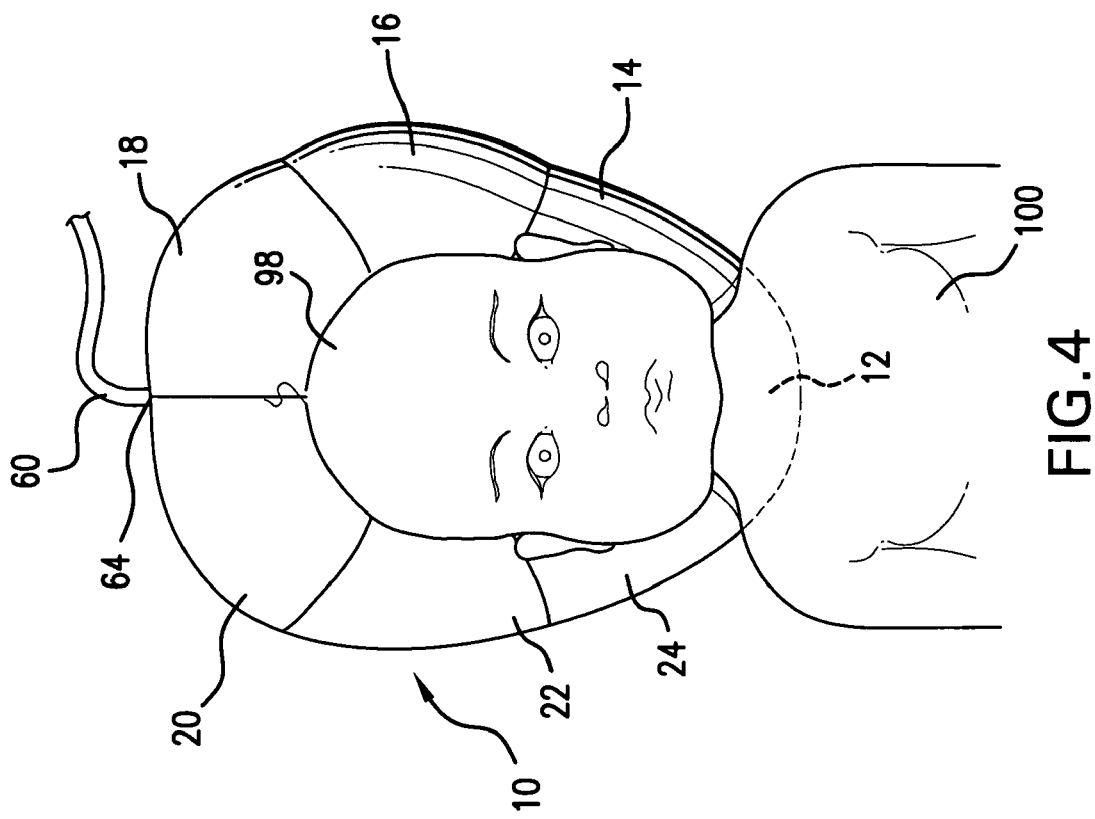
FIG. 4 is a top plan view of an infant's head resting upon the dynamic infant head support.

FIG. 4 is a top plan view of the dynamic infant head support, or pillow, 10. The head 98 of an infant 100 is placed in opening 44 defined in the interior of head support 10. One side of the head 98 of infant 100 contacts compartments 14, 16, 18, while the opposite side of head 98 contacts compartments 20, 22 and 24. The neck of the infant rests upon compartment 12. The selective, and sequential, inflation of the compartments within head support 10, by the selective clamping and unclamping of the several branch tubes, imparts a gentle lifting and turning movement to head 98 of the infant, to counteract any deformational pressures upon the head. Optional projections 46, shown in FIG. 1A, provide a gentle massaging action to the scalp and stabilize the head as it is being lifted and turned slightly. As previously mentioned, it is desirable to heat the delivered air to warm and calm the infant. FIG. 4 also shows the location of conduit 60 as the conduit enters the support 10 via inlet port 64 to join manifold 50 as it would be arranged in the preferred embodiment.

Figure 5:
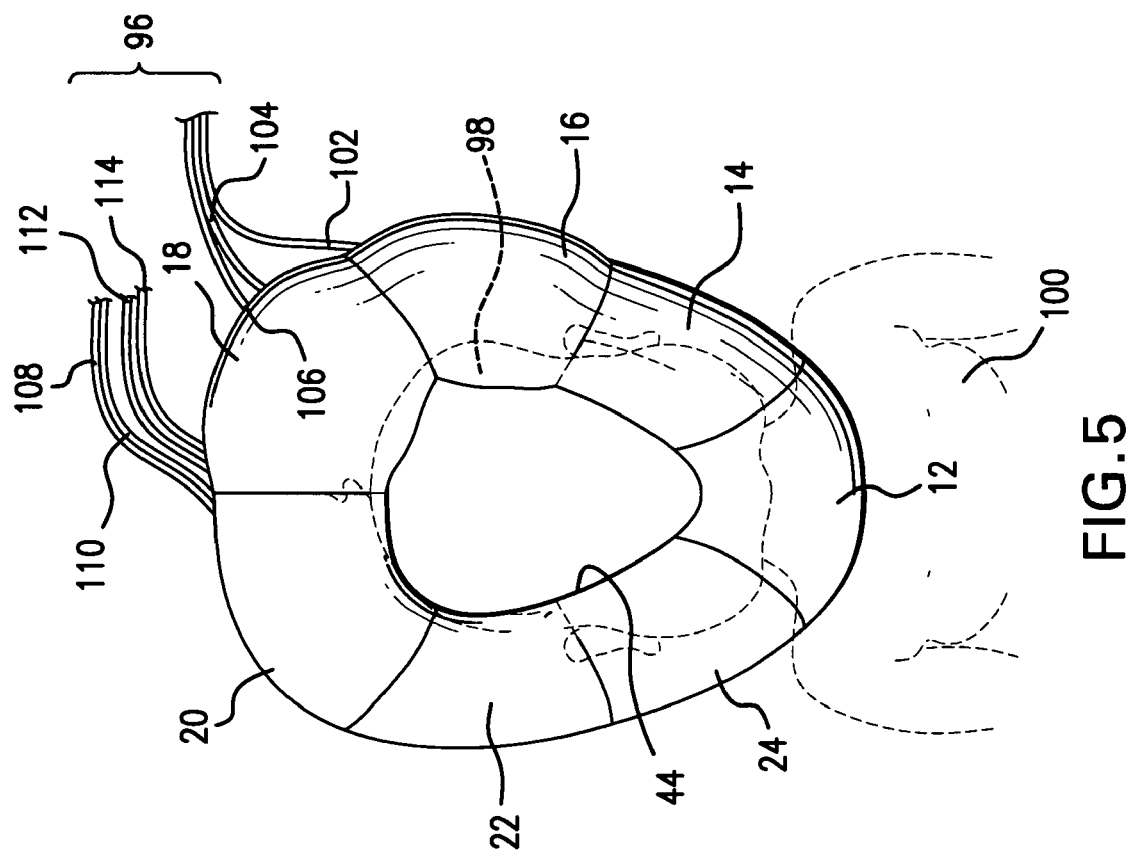
FIG. 5 is a bottom view of an infant's head resting upon the dynamic head support.

FIG. 5 is a bottom plan view of the head support of FIG. 4, with head 98 of infant 100 resting in central opening 44. The neck of the supine infant rests upon compartment 12. A sling (not shown) may extend loosely across opening 44 to provide supplemental covering for head 98 of infant 100. This figure further exhibits the implementation of conduit 96 (shown generally in FIG. 2), which comprises seven lead lines 102, 104, 106, 108, 110, 112 and 114. Electrical lines, or leads, 102, 104 and 106, extend into compartments 14, 16, and 18 to operate valves 74, 78 and 82, respectively. Electrical lines, or leads, 108, 110, 112 and 114, extend into compartments 20, 22, 24 and 12, to operate valves 86, 90, 94 and 70. The electrical circuitry and the pneumatic circuitry are operated, in an interrelated, cooperative manner by controller 62, of conventional design. The sequence for selectively inflating and deflating the compartments within head support 10 is determined by controller 62.

Figure 6A:
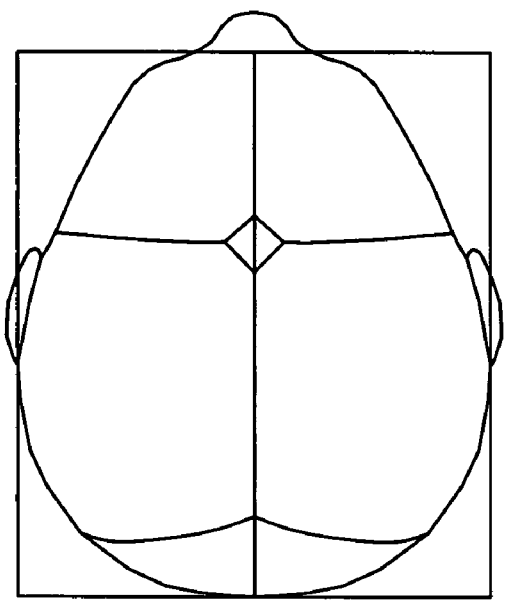
FIG. 6A is a top plan view of the head of a normal infant.
Figure 6B:
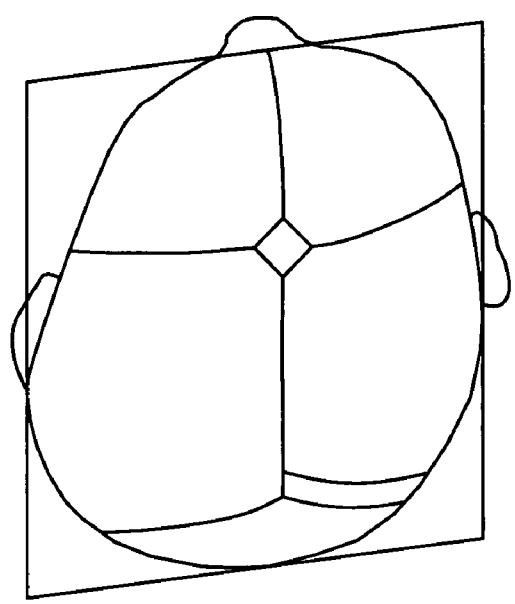
FIG. 6B is a top plan view of the deformed head of an infant.

FIG. 6A is a top plan view of a properly formed head of an infant, while FIG. 6B is a top plan view of a deformed head of an infant. Head support 10 is designed to prevent and/or correct the deformed head of FIG. 6B, without resort to orthotics and/or surgery.

Figure 7:
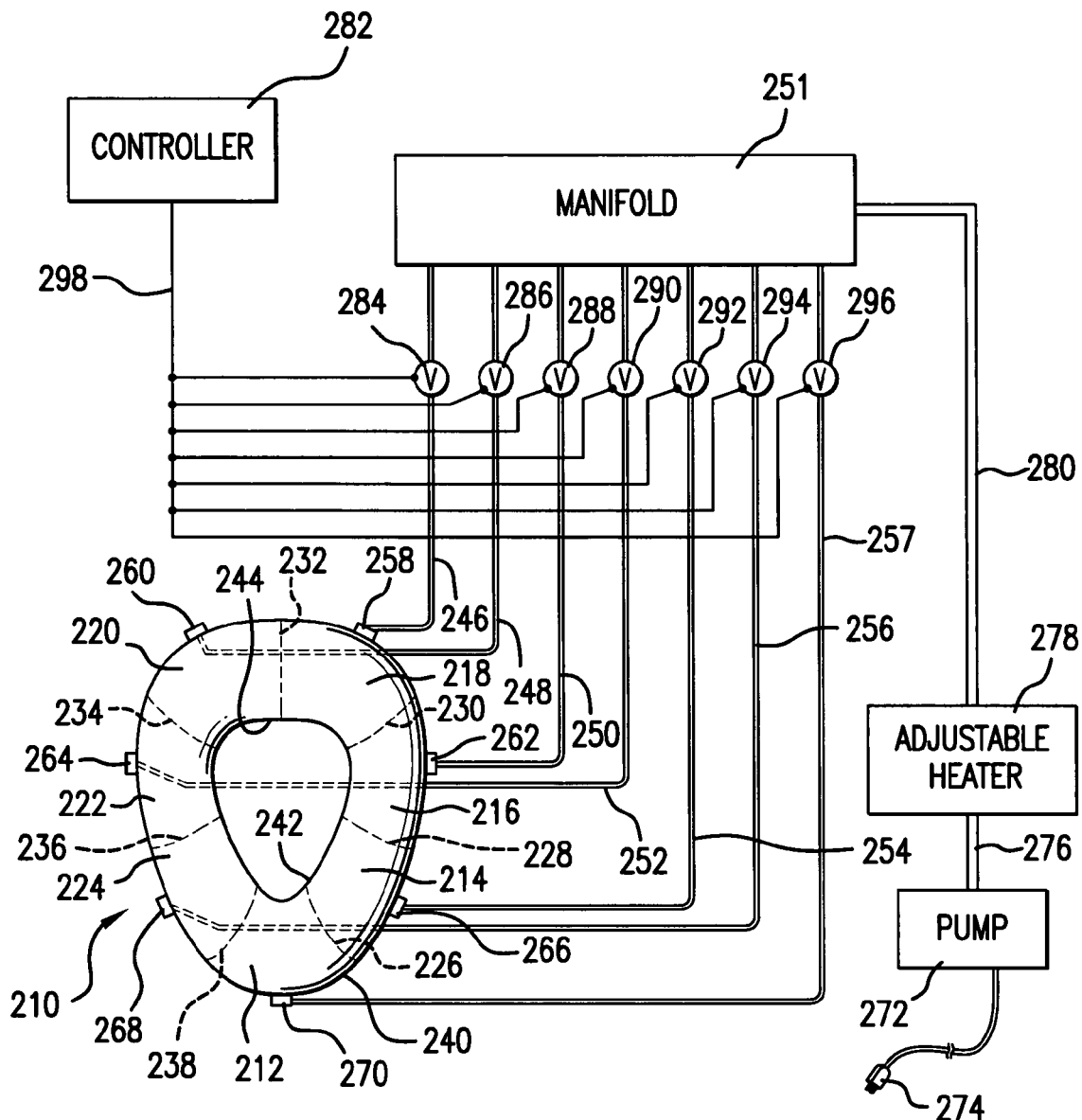
FIG. 7 is a schematic view of a first alternative embodiment of a system for inflating the dynamic infant head support of FIG. 1.

FIG. 7 is schematic view of a first alternative embodiment of the dynamic infant head support system. Support 210, is an oval ring or doughnut-shaped pillow, including seven compartments 212, 214, 216, 218, 220, 222 and 224. Barriers 226, 228, 230, 232, 234, 236 and 238 separate the compartments from one another. The dimensions of each compartment are defined by a first barrier, a second adjacent barrier, an outer wall and an inner wall. Compartment 212, by way of illustration, is defined by barrier 238 and barrier 226, and by outer wall 240 and inner wall 242. An oval-shaped opening 244 is formed in the interior of head support 210. The oval shape of head support 210 ensures that compartment 212, at the base of the support, adequately supports the neck of an infant in supine position.

FIG. 7 further depicts the system for selectively, and sequentially, inflating the individual compartments 212, 214, 216, 218, 220, 222 and 224 within head support 210. Manifold 251 is positioned externally of support 210, in contrast to the location of manifold 50 within support 10, in the preferred embodiment of FIGS. 1-5. Branch tubes 246, 248, 250, 252, 254, 256, and 257 extend from manifold 251 to couplings 258, 260, 262, 264, 266, 268, and 270, distributed about support 210. One coupling is operatively associated with each compartment within support 210, so that the compartments are individually inflated and deflated.

The system for pressurizing head support 210 includes pump 272, which receives power from plug 274 inserted into an electrical receptacle (not shown), conduit 276 which delivers the pressurized air from pump 272 to heater 278, and central tubing 280 which delivers the air to manifold 251 for distribution to the pillow compartments.

Controller 282 includes a program (not shown) for operating the solenoid valves connected to manifold 251 in a predetermined pattern. The solenoid valves are identified by reference numerals 284, 286, 288, 290, 292, 294 and 296. The controller operates the solenoid valves in a particular pattern or sequence, for specific durations of time, so that each compartment within head support 210 may be individually pressurized. The solenoid valves may be operated by remote electrical signals passing from controller 282 via electrical conduit 298, in a known manner.

The solenoid valves are normally biased closed, thus retaining head support 210 in a deflated condition. Upon opening any one of the solenoid valves, the pressurized air fills the related branch tube and the associated compartment. To illustrate, if solenoid valve 284 is opened via a signal from controller 282, the pressurized air from manifold 251 flows through branch tube 246 and coupling 258 to fill compartment 218 and inflate same. Similar relationships hold true for filling compartments 220, 222, 224, 212, 214 and 216 and the related branch tubes and couplings.

Pump 272 also governs the deflation of the selected compartment in head support 210. Pump 272 is reversible in operation, and withdraws air from an inflated compartment to deflate same. The air withdrawn from the selected compartment via the couplings and branch tubes and manifold 251 is coordinated with the opening and closing of valves in each compartment.

Figure 8:
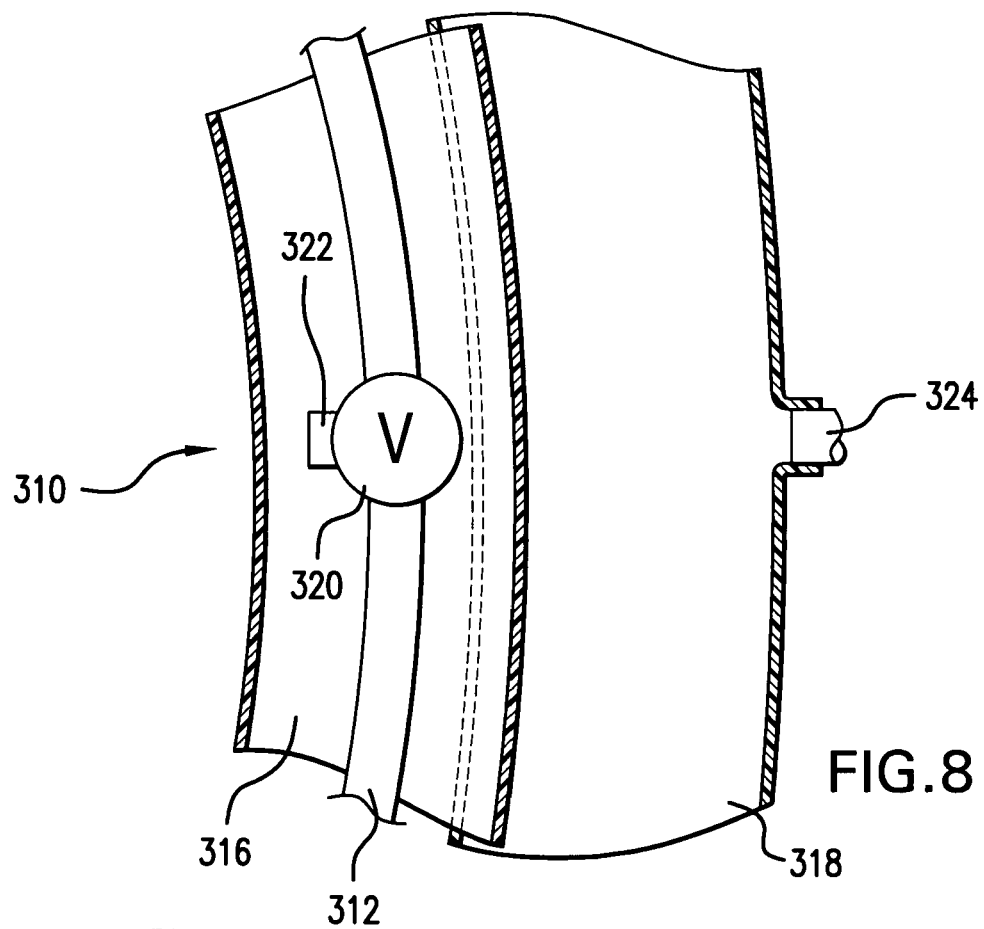
FIG. 8 is a fragmentary view of a second alternative embodiment of a system for inflating the dynamic infant head support(s)
Figure 9A:
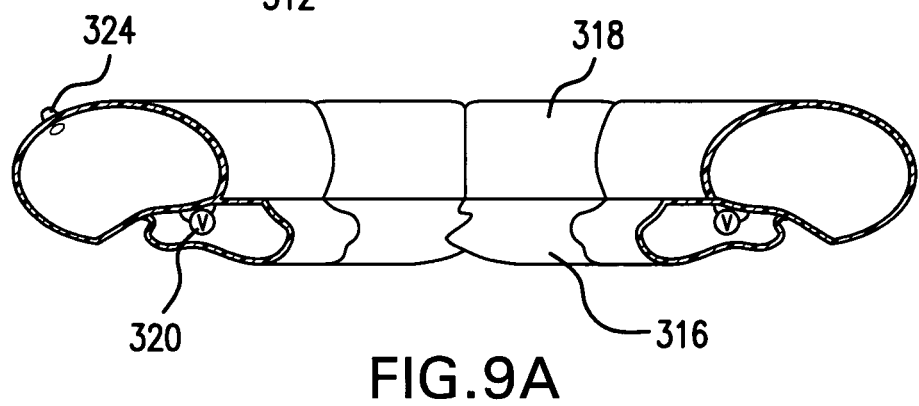
FIG. 9A is a vertical cross-sectional view of the head support of FIG. 8, showing the outer head support in fully inflated condition while the inner head support lies below within the central opening of the outer head support.
Figure 9B:
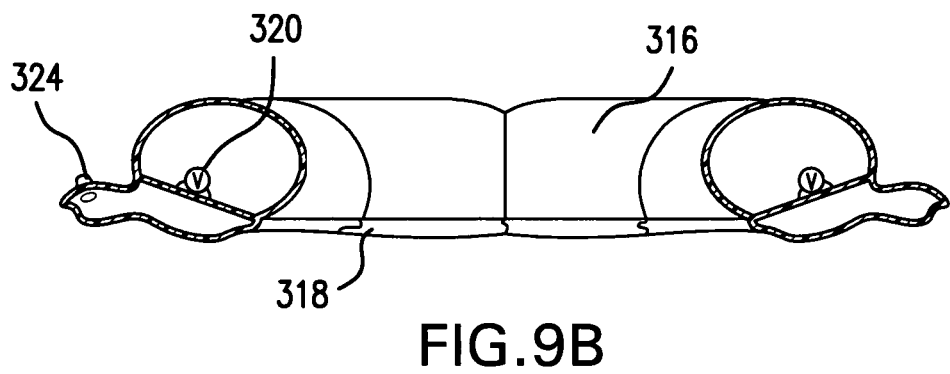
FIG. 9B is a view of FIG. 9A inverted, showing the inner head support in fully inflated condition atop the deflated outer head support.

FIGS. 8-9B illustrate a second alternative head support, indicated generally by reference numeral 310. Whereas head support 10, of the preferred embodiment of FIGS. 1-5, and head support 210, of the first alternative embodiment of FIG. 7, each utilize one manifold, head support 310 employs two distinct pillow systems concentrically paired together. Interior manifold 312 is operatively associated with oval or doughnut-shaped pillow 316, while an exterior assembly (not shown) of manifold, valves and branch tubing is operatively associated with oval or doughnut-shaped pillow 318. Solenoid valve 320 clamps, and unclamps, branch tube 322 to regulate the flow of pressurized air into a compartment within the inner pillow 316. The outer pillow operates in a similar fashion to that of the first alternative embodiment detailed in FIG. 7. Coupling 324, associated with a compartment of pillow 318, is included in the drawing. The advantage of pairing different-sized, complete head supports together is the ability to service numerous patients, with diverse head sizes, with the availability of a single, readily adaptable device.

Yet other refinements and improvements to the dynamic head support may occur to the artisan skilled in the pertinent fields of endeavor. For example, the program (not shown) within controller 62 may have a constant or adjustable sequence setting and preset inflation/deflation durations, or these features may be customized by the purchasing institution, such as a hospital. Head support 10 or 210 may be produced in varying sizes appropriate for premature infants and children up through 12 months of age, based on normalized circumference growth chart averages, or consist of two or more concentric pillow systems in one device such as head support 310. The shape of the pillow and the central opening therein may be altered; while an oval shape is shown, a doughnut-shaped, round or even modified horseshoe-shaped pillow will function satisfactorily.

Instead of air, the head support system may utilize a gel, a liquid or other fluid, or mechanical devices, to inflate or expand the compartments within the head support. A battery power source may replace the plug and electrical receptacle for delivering power to the system for inflating and deflating the head support. The plug cord may be of a predetermined length or of a known retractable design. The power switch may be illuminated or activated and deactivated by remote control.

The present invention could be used in conjunction with a stabilizing wedge for the shoulders or torso, thereby reducing the possibility of infant-initiated rotation to prone position, a potential suffocation risk. Although the invention has been exemplified by showing seven compartments, the pillow may include more or less than seven compartments without departing from the teachings of the invention.

Consequently, the appended claims should be liberally construed in a manner consistent with the considerable scope of the present invention, and should not be restricted to their literal terms.

What is claimed is:

1. A dynamic head support system comprising:
a) an inner and an outer doughnut-shaped pillow,
b) the outer pillow being larger in size than the inner pillow,
c) the pillows being joined together in concentric fashion, with a central opening to receive the head of a patient while portions of the pillows which surround the opening support the head of the patient,
d) the outer pillow being elevated in relation to the inner pillow,
e) a plurality of barriers disposed at spaced intervals about the interior of said pillows to divide the pillows into separate compartments,
f) a plurality of couplings, one coupling operatively associated with each compartment;
g) a manifold associated with each pillow,
h) a plurality of branch tubes extending between said manifold and said couplings on said pillow,
i) a plurality of valves, one valve being secured to each one of said branch tubes,
j) means for introducing fluid into said manifold for distribution into said plurality of branch tubes,
k) said means including a controller for operating said valves in a predetermined sequence for opening and closing said branch tubes to inflate or expand and deflate or contract selected ones of said compartments, within said head support, thereby gently lifting and turning slightly the head of the patient to prevent, or alleviate, head deformation.

\* \* \* \* \*